United States Patent [19]

Berarducci

[11] Patent Number: 4,727,895
[45] Date of Patent: Mar. 1, 1988

[54] DENTAL FLOSS APPLICATOR

[76] Inventor: James P. Berarducci, 6340 Pottsburg Plantation Blvd., Jacksonville, Fla. 32216

[21] Appl. No.: 859,367

[22] Filed: May 5, 1986

[51] Int. Cl.$^4$ .............................................. A61C 15/00
[52] U.S. Cl. ....................................................... 132/91
[58] Field of Search .............. 132/89, 91, 92 R, 92 A, 132/93; 433/130

[56] References Cited

U.S. PATENT DOCUMENTS

| | | | |
|---|---|---|---|
| 158,377 | 1/1875 | Hickman | 433/130 |
| 3,835,872 | 9/1974 | Daniel | 132/92 R |
| 3,908,677 | 9/1975 | Beach | 132/92 R |
| 4,005,721 | 2/1977 | Yasumoto | 132/91 |
| 4,245,658 | 1/1981 | Lecouturier | 132/92 A |
| 4,315,517 | 2/1982 | Krag | 132/89 |

Primary Examiner—Robert Peshock
Assistant Examiner—Adriene J. Lepiane
Attorney, Agent, or Firm—Arthur G. Yeager

[57] ABSTRACT

A dental floss holder for readily applying floss to teeth includes a pistol grip offset handle with an arm extending angularly forward of the handle top and a post extends laterally of the handle bottom, a thimble at the end of the arm is engaged by the index finger, a receiving ring is located forwardly of the thimble and a floss stretching member is selectively rotatably positionable in such member having two spaced upstanding fingers with a loop end of floss engaged thereon and passing through the ring and another loop end about the post on the handle and adapted to be stretched taut by squeezing the floss between its ends towards the handle by the user's fingers and a lip retractor is included on the flossing head.

35 Claims, 15 Drawing Figures

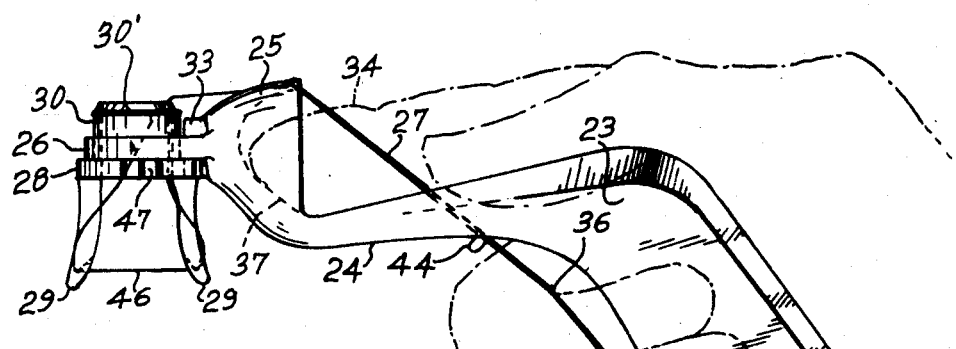
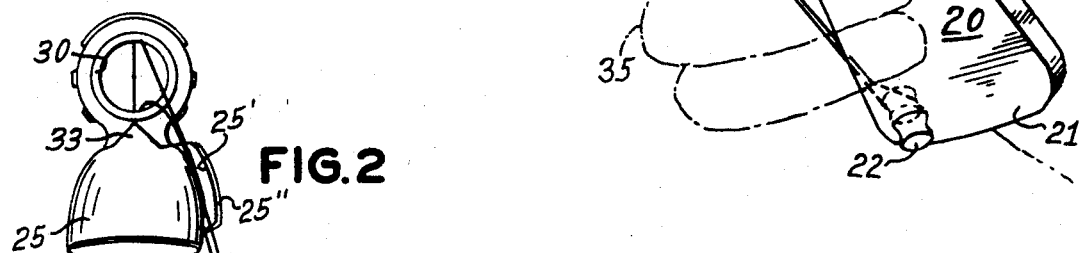
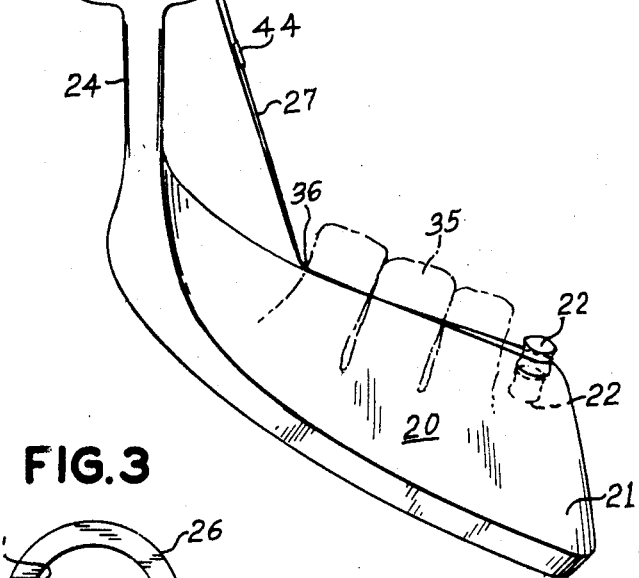
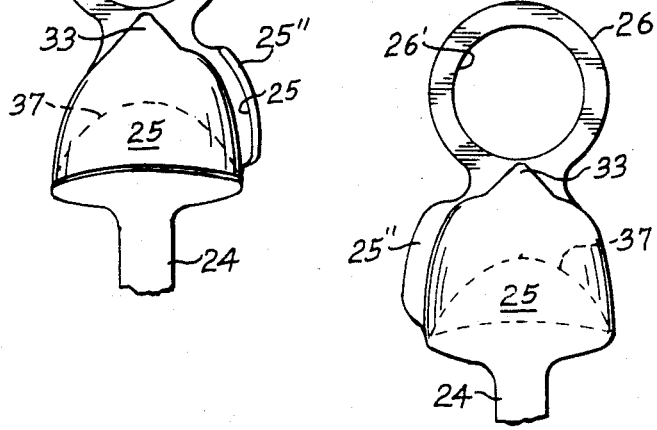
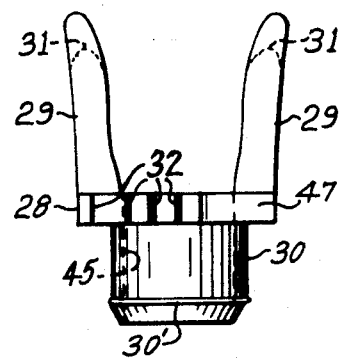
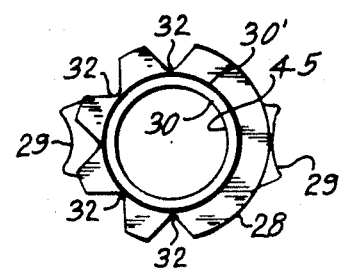

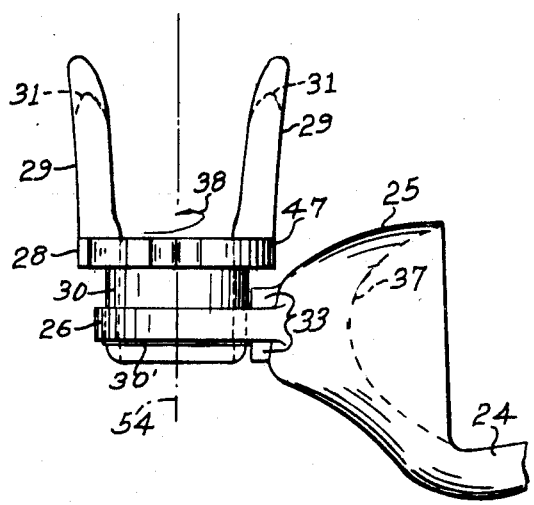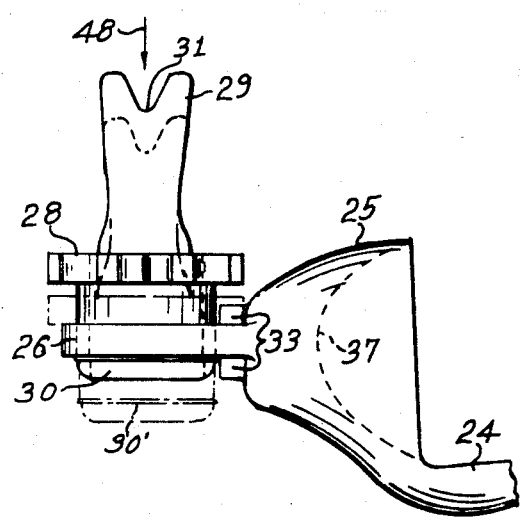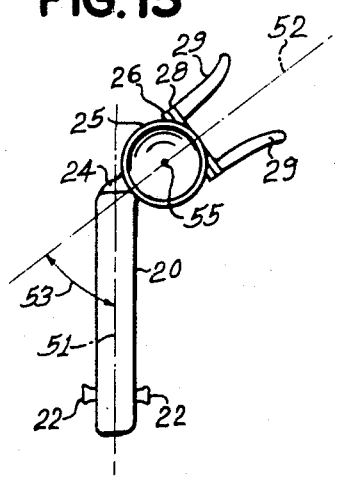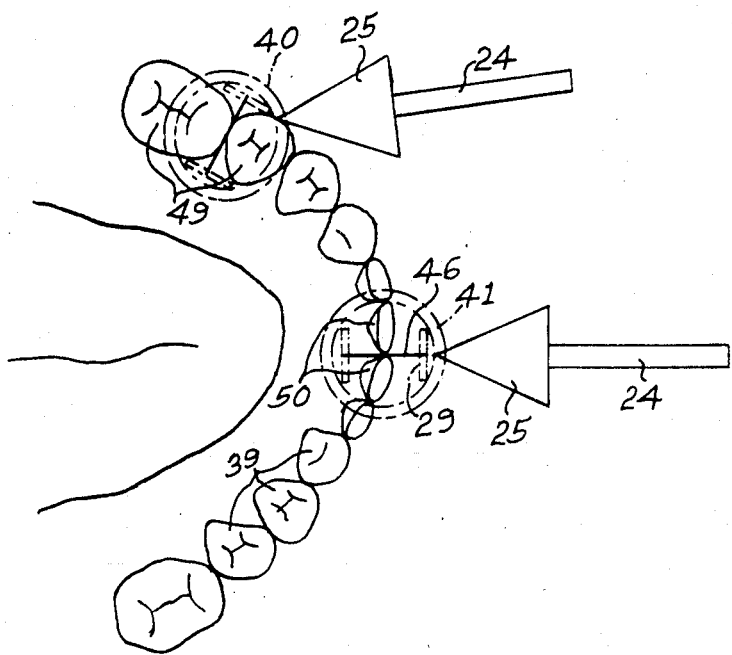

DENTAL FLOSS APPLICATOR

BACKGROUND OF THE INVENTION

Dental flossing of teeth has long been a recommended procedure to keep teeth clean and minimize the formation of plaque. Because it is awkward and unpleasant to use ones fingers to hold the floss taut while applying it to teeth, there have been many floss holders which have appeared in the patent and hygienic art over the years. Most of such devices have been designed to be small enough to insert comfortably in the mouth and provide a short taut length of floss which can be applied to the spaces between teeth where food particles are found. Most of the prior art devices are difficult to load with floss, especially if the floss tears and requires reloading through the head. Some of such devices have been adjustable to provide different angles of attack without changing the general position of the hand holding the device. None of these devices has proved to be widely accepted because none has provided all of the convenience that the public desires nor do they provide proper application of the floss to the teeth. In accord with this invention the applicator overcomes many objections to the prior art devices and provides those conveniences desired by the users and is an efficient tooth cleaning implement.

It is a general object of this invention to provide a novel improved dental floss applicator. It is another object of this invention to provide an adjustable easily manipulated dental floss applicator for cleaning teeth. A specific object is the provision of an applicator easily loaded with a floss loop and which also provides clean floss sections by merely advancing the loop. Still other objects will become apparent from the more detailed description which follows.

SUMMARY OF THE INVENTION

In one aspect of this invention a dental floss applicator includes an L-shaped body including an elongated pistol grip handle having an upper and a lower end portion and an elongated arm having an end portion affixed to and extending forward from the handle upper end portion. A floss engaging post means projects laterally outwardly from the handle lower end portion about which a floss loop end portion engages. A support means is rigidly attached to the opposite arm end portion and a floss stretching member is removably attachable to such support means. The floss stretching member includes a base, preferably an annular base, positioned on the support means, preferably a ring support member, and two upwardly extending fingers attached to diametrically opposite sides of the base, each of such fingers having a V-shaped depression in the upper extremity thereof adapted to receive a spanning loop end portion of floss therebetween.

In other aspects selective means are provided for releaseably connecting the floss stretching member to the support means in a plurality of selected fixed orientations. The selective means for releaseably connecting includes means on the support means and cooperating means on the base to selectively orient the base in a plurality of radially different positions of the floss stretching member to accommodate the various positions of teeth in a user's mouth. Preferably, one of such means and cooperating means includes a shoulder and the other such means and cooperating means includes a pair of shoulders engageable with the aforesaid shoulder and preventing relative rotation between the support means and the base while so engaged. The cooperating means is defined by a plurality of notches in the perimeter of the base, and the one such means includes at least two spaced projections, one of which interfits with one of the notches when the floss stretching member is in an upright position and the other of which interfits with one of the notches when the floss stretching member is in a downright position.

Further aspects of the invention are seen wherein the handle is offset so that a central plane through the handle and arm is at an acute angle, preferably about 30°–60°, to a plane through the longitudinal axis of the arm and floss stretcher to provide a comfortable position for a hand of a user during flossing of a user's teeth. The stretching member has a passageway therethrough between the fingers and an elongated continuous loop of dental floss stretched spanningly over said V-shaped depressions of the fingers and through the passageway and about the floss engaging post permitting a user to grip the floss loop adjacent to and forced toward the handle whereby the floss is stretched taut between the V-shaped depressions of the fingers. Preferably the loop of dental floss includes a tab attached to the loop to permit a user's fingers to grip same and advance or retract the floss in either direction between the fingers while the floss is not taut, thereby placing a clean floss section between the floss head fingers.

Additional aspects are provided in the preferred embodiment of the applicator in which the support means includes a thimble openingly facing toward the handle and adapted to be engaged with the fingertip of the index finger of the user's hand gripping the handle. The thimble has a guideway engageable by the floss when the stretching member is located in a downright position so that the floss may be looped about another post means on the handle projecting generally in alignment with the aforementioned post means.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the dental floss applicator of this invention to floss the lower teeth of a user and showing in broken lines the hand of the user gripping the applicator and floss to tension same.

FIG. 2 is a top plan view of the applicator in FIG. 1;

FIG. 3 is an enlarged top plan view of the forward end of the applicator without the floss stretching member shown in FIGS. 1 and 2;

FIG. 4 is a bottom plan view of the applicator of FIG. 3;

FIG. 5 is an enlarged front elevational view of the floss stretching member shown in FIGS. 1 and 2;

FIG. 6 is a bottom plan view of the floss stretching member of FIG. 5;

FIG. 7 is an enlarged partial elevational view of the thimble, ring support, and floss stretching member showing the member in an upward position for subsequent rotation and/or moved into its locked position to floss the upper teeth;

FIG. 8 is a view similar to that of FIG. 7 with the floss stretching member shown as partially removed from the ring support to clear the locking means and rotated to a position about 90° with respect to FIG. 7;

FIG. 9 is a simplified schematic illustration of the applicator employed to clean teeth at various positions of the floss stretching member and angles of the floss thereon;

FIG. 15 is a reduced rear elevational view of the floss applicator shown in FIG. 10 with the arm upper edge between the handle and the thimble being perpendicular to the drawing.

DETAILED DESCRIPTION OF THE INVENTION

Figure 10:
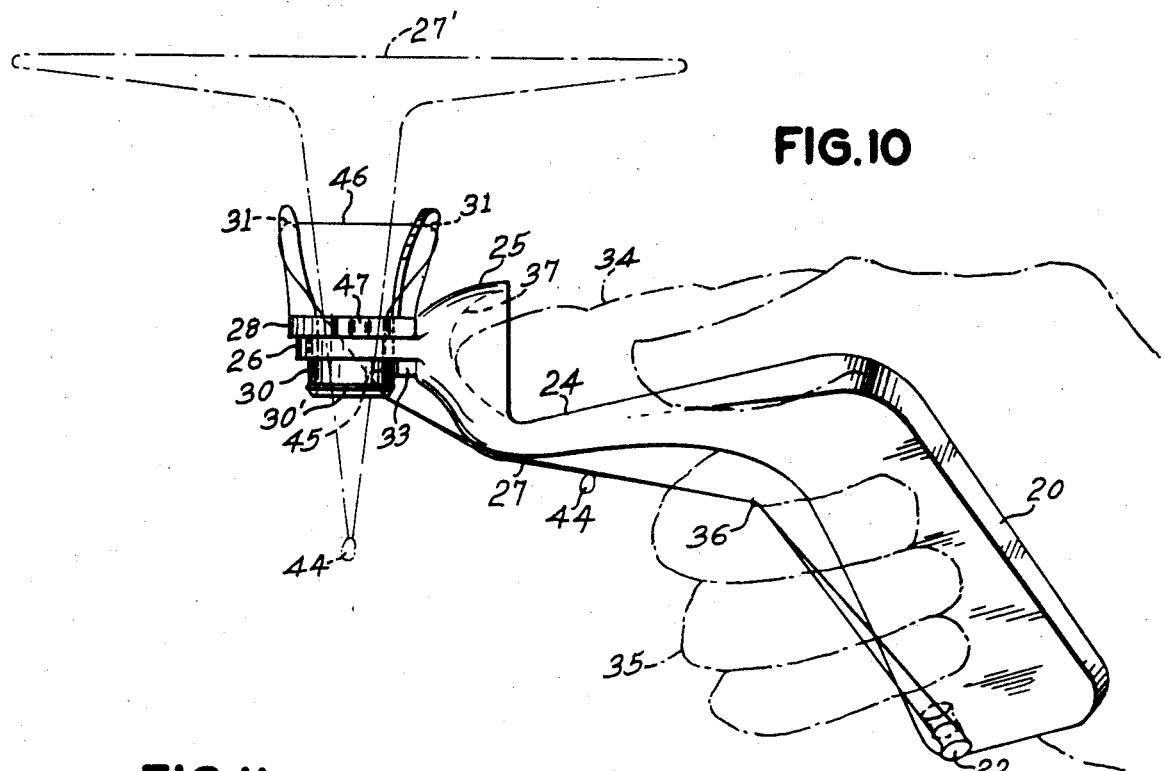
FIG. 10 is a view of the applicator similar to FIG. 1 showing a floss loop attached to the applicator and drawn taut and with another embodiment of a head, according to this invention, shown in upright position.
Figure 11:
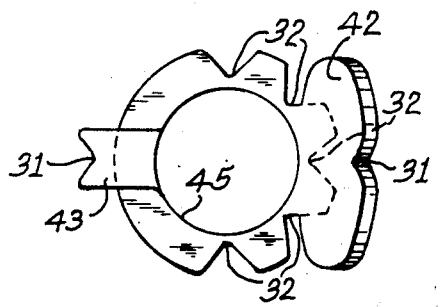
FIG. 11 is a top plan view of the floss stretching member of the head shown in FIG. 10 and depicting the lip retractor.
Figure 12:
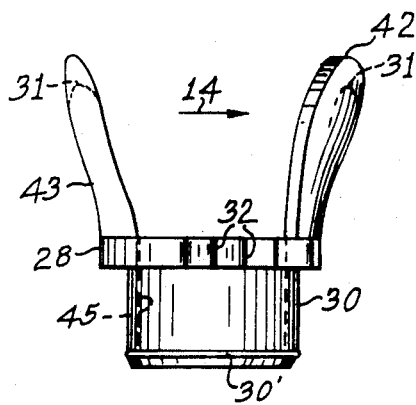
FIG. 12 is a front elevational view of the member shown in FIG. 11.
Figure 13:
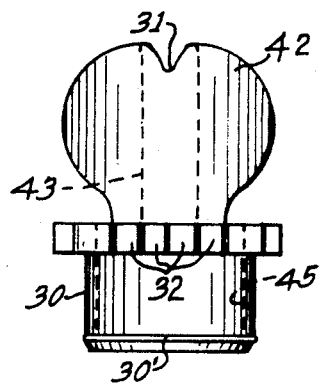
FIG. 13 is an outer side elevational view of the member shown in FIG. 11.
Figure 14:
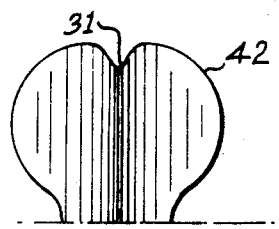
FIG. 14 is an inner partial side elevational view of the lip retracting finger of the member shown in FIGS. 11–13.

The overall structural features of one embodiment of this invention can best be understood by reference to FIGS. 1–6. A pistol grip elongated handle 20 is shown being held by the hand of the user (in broken lines). Handle 20 has a lower end portion 21 and an upper end portion 23, and projecting outwardly from lower end portion 21 in a lateral direction is post means in the form of generally aligned stub posts 22 which are used to hold one end portion of a loop of floss 27 for purposes that will be described in greater detail below. Adjacent handle upper end 23 an arm 24 extends forward and generally at a right angle with respect to handle 20 in substantially the same manner that the barrel of a pistol extends forwardly of the grip but the handle is not aligned with or is offset from the arm. At the forward end of arm 24 is a cup or thimble member 25 opening toward the handle and adapted to receive the tip of the index finger 34 of the user within the recess 37 of member 25. At the forward side of thimble member 25 is a support means in the form of a support ring 26 rigidly attached to thimble member 25 and having a central opening 26' therein. Floss stretching member 28 is removably attachable in a plurality of rotative and fixed orientations in opening 26' of ring support 26. Member 28 is the operational end which extends into the user's mouth and holds the flossing material of this invention and is designed to have several selected positions to provide convenience and proper positioning of the flossing material to the user in cleaning teeth and without materially changing the positioning of the hand gripping the handle of the device as will be more clearly understood hereafter.

Floss stretching member 28 has an annular base 30 which is supported by the support means by interfitting concentrically inside ring support 26. A shoulder means 30' may be provided on base 30 short of the end so that base 30 may be "snapped" into ring 26 and yet readily removed therefrom to change between upright and downright positions for member 28. Member 28 may be manually rotated within ring 26, upon an initial unlocking release (later described), to several different positions, and additionally base 30 may be inserted into ring support 26 from either side to permit the operational parts of member 28 to project upwardly or downwardly from ring support 26. The view of FIG. 1 shows member 28 pointing downwardly to clean the lower teeth.

Floss stretching member 28 includes two fingers 29 projecting upwardly from annular base 30 on diametrically opposite sides of base 30. Each finger 29 has a floss engaging groove 31, e.g., a V-shaped notch or depression, in the middle of its upper bifurcated edge. It is between these two grooves or notches 31 that floss is stretched taut so as to be applied to the teeth. As seen in FIGS. 1 and 2, when stretcher 28 is in its downright position, floss 27 extends through guideway 25' formed by flange 25" on the upper right portion of thimble 25 as shown in FIG. 2 and looped about the right projecting post 22.

In order for member 28 to be adjustable to different selected radial positions, selective locating means are provided in the form of shoulders or several notches 32 in member 28 which interfit with shoulder means in the form of lug 33 affixed to ring support 26. It is, of course, fully evident that notches 32 may be located on ring support 26 and lug 33 on member 28 without departing from the scope of this invention. Floss stretching member 28 may be positioned at different orientations with respect to ring support 26 by raising member 28 upwardly into the full line position shown in FIG. 8 and then rotated in the direction of arrow 38 shown in FIG. 7 and then pushed down into its broken line position shown in FIG. 8. Therefore, different orientations of member 28 will change its relative position with respect to thimble 25, arm 24, and handle 20 which are unitarily formed. Notches 32 and lug 33 are provided for interfitting with each other regardless of whether member 28 is inserted into ring support 26 in upright or downright positions shown respectively in FIGS. 10 and 1. One preferred structure is to provide for the lug 33 to be on both sides of ring support 26 as shown in FIGS. 3 and 4 and to provide base member 30 with a flange 47 (see FIG. 5) into which notches 32 are formed. Thus, whichever direction base member is introduced into ring 26 there will be notches 32 in flange 47 to mate with a lug 33.

In FIGS. 11–14 a preferred embodiment of floss stretching member 28 is illustrated in which one of the upstanding fingers 42 is curved and broad while the other finger 43 is narrow and substantially the same as finger 29. Both of fingers 42 and 43 have a V-notch or depression in the middle of the upper edge of the respective fingers to serve as a guide for stretching floss between the fingers and to inhibit lateral displacement of the floss therefrom. Broad faced finger 42 is positioned on the side of member 28 which will be next to the lip of the user, i.e., above and centrally of notches 32, and the broad face will serve as a lip retractor to prevent any pinching or unintentional abrasion to the lining of the lip and mouth when using the floss applicator of this invention. As may be seen the finger 42 generally has a central portion conforming to finger 43 and a pair of side flange portions curved inwardly and smoothly rounded to form a generally heart shaped lip retractor.

In the use of this applicator the hand position of the user remains substantially the same regardless of whether the upper teeth or lower teeth, the molars or incisors are being flossed. Thus, if one is right handed there is no need to floss some teeth with the left hand, which might be awkward for a right handed person. For upper teeth the floss stretching member 28 is positioned such that fingers 29 are upright as in FIGS. 7 and 8. For lower teeth the floss stretching member 28 is positioned such that fingers 29 are downright as in FIGS. 1 and 2. Once the upward or downward position is chosen, floss stretching member 28 is adjusted angularly or rotatively by partially inserting annular base member 30 into ring support 26 and rotating member 28 as in the direction of arrow 38 of FIG. 7 until the desired orientation of fingers 29 is achieved. Member 28 is then fixed in place by fully inserting base member 30 in the direction of arrow 48 into ring support 26 as shown in broken lines in FIG. 8. This permits lug 33 to fit into the nearest notch 32 to prevent further rotational movement of member 28 with respect to ring support 26. As shown in simplified illustration of FIG. 9, the direction of thimble 25 and extension arm 24 of the floss applicator may be kept at generally the same angle of approach to teeth 39 regardless of whether the applicator is used to clean molars 49 or incisors 50. All that needs to be done is to adjust the positioning of floss stretching member 28 with respect to ring support 26, as described above. This should alter the position of member 28 from that shown at 40 to that shown at 41 for convenience and more effective working of the floss between the teeth in these two positions in the mouth and the teeth therebetween.

In accord with the preferred embodiment, a closed loop of floss 27 having a tab 44 attached thereto is used to advance or retract such floss. The length of the loop is such that one end is spanningly stretched across notches or depressions 31 and the other end is looped over post 22 at the bottom end 21 of handle 20 with just enough slack for easy attachment at these two ends, and yet by gripping by the fingers 35 of the hand of a user toward handle 20, the floss loop is pulled at 36 to cause a taut length 46 between notches 31 on the stretcher member 28. Member 28 is annular with a passageway 45 therethrough between the fingers 42 and 43, as seen in FIG. 10 and floss 27', shown in broken lines, is inserted through passageway 45, with one end stretched across notches 31 and the other end over post 22, as shown by solid lines 27 in FIG. 10. Tab 44 is a convenient location index for moving the floss manually to advance or retract the floss. After using the floss at one position between the floss head finger pairs 42 and 43, or 29 for cleaning teeth, it usually is preferred or desirable to move the floss a small distance, i.e., one-half inch, to a new, unused portion for cleaning the next location. Tab 44 may be easily pulled in either direction to bring a new section of floss loop 27 between notches 31 by merely releasing the floss by the hand of the user and using the other hand to grip tab 44 and move the floss accordingly. Also, the handle 20 may be hollow with a releasable closure into which many floss loops 27 may be stored.

In FIG. 15 the handle 20 and the floss stretcher 28 are angularly disposed with respect to each other for a more comfortable hand and arm position. A central plane 51 passing through handle 20 and extension arm 24 is at an included acute angle 53 with respect to a plane 52 containing the longitudinal axis 54 (see FIG. 7) through floss stretching member 28 and central axis 55 of thimble 25. This offset arrangement provides a more natural positioning of the index finger to be seated in thimble 25 and thereby relaxes the wrist of the user. It is to be understood, however, that the scope of this invention is not in any way limited to such positions of thimble 25 and floss stretching member 28 with respect to plane 51. For example, for a left-handed user the most comfortable position is a mirror image of FIG. 15 with plane 52 angled to the left of plane 51. While a simpler design may provide for the plane 52 and plane 51 to be coincident, such design would not be as satisfactory.

Even a simpler design may be provided by eliminating the thimble 25 entirely, such design is not preferred in that users have much better control and are familiar with using the index fingers for applying the force necessary to move the taut floss between teeth and this invention permits a similar action but with only one finger needed for such control, etc. Another possible alteration is to employ another style of handle 20 which is not a pistol grip, but again the pistol grip is preferred to provide a comfortable position for the hand of the user to manipulate the floss in cleaning teeth. However, if space and size are important, clearly smaller handles may be used in place of the generally full sized pistol grip design shown herein.

As is now determinable from the above described details of the invention a novel dental floss applicator is provided in which an elongated handle having lower and upper end portions is connected at its upper end to the rearward end portion of an elongated arm and the forward end portion being connected to a support means. A generally horizontal axis extends between the arm end portions with the handle extending downwardly and laterally of such horizontal axis. A selectively attachable floss stretcher includes a base member positioned on the support means in an upright position and alternately in a downright position, and a pair of spaced oppositely facing generally vertical finger members project from the base member and have bifurcated free ends adapted to receive floss therein. Selective locating means are provided between the base member and the support means to selectively orient the base member in various rotative positions with respect to the support means in either the upright and downright positions. Preferably the support means includes a thimble member attached to the arm forward end portion and such thimble member has a cavity therein opening rearwardly to receive an index fingertip therein of a hand gripping the handle. The handle includes a post means projecting laterally from the handle lower end portion to receive part of a dental floss therearound. The base member includes a generally vertical passageway therethrough between the finger members through which a part of a dental floss extends. An elongated continuous loop of dental floss includes a first loop end portion spanning between the finger members and two portions passing through the base member passageway in and extends adjacent the handle. A second loop end portion of the floss is engaged about the post means. The two portions of the floss are gripped by a hand of a user simultaneously with gripping of the handle, with the index fingertip in the thimble, to cause the first loop end portion to be tightly stretched between the finger members. A tab is connected to the floss to advance and retract the floss when untaut. The support means includes a ring member and the selective locating means includes at least one shoulder means and at least two shoulder means cooperating with the one shoulder means with such shoulder means being carried by the base and support member. Normally the one shoulder means is attached to the support member and the two shoulder means is attached to the base member. Preferably, the one shoulder means includes a pair of spaced projections and at least two shoulder means includes a plurality of spaced notches, one of the pair of projections engaging any one of the notches when the stretcher is in the upright position and the other of the pair of projections engaging any one of the notches when the stretcher is in the downright position. It is preferred that one of the finger members be narrow with generally upright and parallel side edges which are smoothly rounded and a V-depression in the middle portion of the upper edge thereof while the other of the finger members includes a narrow central portion conforming to the one finger member and laterally extending flanges curved inwardly and forming a general heart shaped lip engaging member with smoothly rounded edges and with a V-notch in the middle portion of the upper edge thereof.

Materials of construction for the applicator of this invention are not limited to any particular type as would occur to those skilled in the art. Preferably, a plastic material should be used and it should be tough, such as a polyacrylate, polymethacrylate, polyacetal, polyamide, polyethylene, polypropylene, and the like, since they will not tend to chip the teeth and will not break easily under normal use.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A dental floss applicator comprising an elongated handle having a lower end portion and an upper end portion, an elongated arm having rearward and forward end portions and a generally horizontal axis passing therebetween, said rearward end portion being connected to said upper end portion of said handle with said handle extending downwardly and laterally of said horizontal axis, a support means attached to and extending forwardly of said arm forward end portion, a selectively detachable floss stretcher having a movable base member positioned on said support means in an upright position and alternately in a downright position, a pair of spaced oppositely facing generally vertical finger members projecting from said base member and having bifurcated free ends adapted to receive floss therein, selective locating means between said base member and said support means to selectively orient said base member in various rotative positions about a generally perpendicular axis to said horizontal axis with respect to said support means in either said upright and downright positions.

2. The applicator of claim 1 wherein said support means includes a thimble member attached to said arm forward end portion and having a cavity therein opening rearwardly to receive an index fingertip therein of a hand gripping said handle.

3. The applicator of claim 1 wherein said handle includes post means projecting laterally from said lower end portion thereof adapted to receive part of a dental floss therearound.

4. The applicator of claim 1 wherein said base member includes a generally vertical passageway therethrough and between said finger members through which a part of a dental floss extends.

5. The applicator of claim 1 wherein said support means includes a thimble member attached to said arm forward end portion and having a cavity therein opening rearwardly to receive an index fingertip therein of a hand gripping said handle, said handle includes post means projecting laterally from said lower end portion thereof adapted to receive a part of a dental floss therearound, said base member includes a generally vertical passageway therethrough and between said finger members through which a part of a dental floss extends, and an elongated continous loop of dental floss having a first loop end portion spanning between said finger members and two portions passing through said passageway in said base member and extending adjacent said handle and a second loop end portion about said post means, said two portions of said floss being adapted to be gripped by a hand of a user simultaneously with gripping of said handle to cause said first loop end portion to be tightly stretched between said finger members.

6. The applicator of claim 1 wherein said support means includes a member, said selective locating means includes at least one shoulder means and at least two shoulder means cooperating with said one shoulder means with such shoulder means being carried by said base and support member.

7. The applicator of claim 6 wherein said one shoulder means is attached to said support member and said two shoulder means is attached to said base member.

8. The applicator of claim 7 wherein said one shoulder means includes a pair of spaced projections, said two shoulder means includes a plurality of spaced notches, one of said pair of projections engaging any one of said notches when said stretcher is in said upright position and the other of said pair of projections engaging any one of said notches when said stretcher is in said downright position.

9. The applicator of claim 8 wherein one of said finger members is narrow with generally upright and parallel side edges which are smoothly rounded and a V-depression in the middle portion of the upper edge thereof, the other of said finger members including a narrow central portion conforming to said one finger member and laterally extending flanges curved inwardly and forming a general heart shaped lip engaging member with smoothly rounded edges and with a V-notch in the middle portion of the upper edge thereof.

10. A dental floss applicator comprising an elongated pistol grip handle having a lower end portion and an upper end portion, a post means projecting laterally from said lower end portion for receiving floss thereabout, and an elongated arm having opposite end portions, one said arm end portion being connected to and extending forward from said upper end portion, a thimble member attached to the other said arm end portion and adapted to receive an index finger tip of a user's hand gripping said handle of said applicator, a support means attached to and extending forwardly of said thimble member, and a detachable floss stretcher positionable on said support means in selected rotative orientations, said stretcher including a base member adapted to fit onto said support means in an upright position and downright position, a pair of finger members projecting generally in the vertical direction from said base member and terminating in a forked configuration adapted to receive a length of floss therein and stretched between said pair of finger members, and notch means between said base member and said ring support for indexing said annular base member in a plurality of radially different positions on said support means.

11. The applicator of claim 10 wherein said handle and said arm define a general plane, said stretcher having a rotative axis generally medially of said finger members with said axis passing through said plane at an angle whereby said handle is offset to provide a comfortable hand position thereof by a user in flossing a user's teeth whether said stretcher is in said upright or downright position.

12. The applicator of claim 11 wherein said angle is between about 30° and 60°.

13. The applicator of claim 10 wherein said notch means includes a plurality of spaced notches around the perimeter of said base member, and said ring support includes a rigid lug adapted to engage with selective said notches.

14. The applicator of claim 10 wherein one of said finger members is narrow with generally upright and parallel side edges which are smoothly rounded and a V-depression in the middle portion of the upper edge thereof, the other of said finger members including a narrow central portion conforming to said one finger member and laterally extending flanges curved inwardly and forming a general heart shaped lip engaging member with smoothly rounded edges and with a V-notch in the middle portion of the upper edge thereof.

15. The applicator of claim 14 wherein said one finger member is located above and remotely from said notch means and said other finger member is located above and adjacent said notch means.

16. The applicator of claim 10 wherein said floss stretcher includes a central passageway extending therethrough and through which the floss extends after spanning between said pair of finger members.

17. The applicator of claim 16 further comprising an elongated continuous loop of dental floss with a tab affixed to said loop, said loop being of a size to extend from a looped end portion spanning between said pair of finger members of said floss stretcher through said passageway and another looped end portion about said post means and capable of being tightened to a taut condition by gripoing with fingers of a user's hand while gripping around said handle, said tab being gripped by user's fingers to advance or retract said floss to a different spanning portion between said pair of finger members.

18. The applicator of claim 10 wherein said thimble includes a guideway engageable by floss when said stretcher is in said downright position.

19. The applicator of claim 18 wherein said post means includes a post extending laterally from each side wall of said handle and being generally aligned, one of said posts being engaged by a floss loop end when said stretcher is in said upright position and the other of said posts being engaged by a floss loop end when said stretcher is in said downright position.

20. The applicator of claim 10 wherein said support means is defined by a ring member having an opening therethrough, said base member including a body portion conforming to said opening in said ring member whereby said body portion snugly and rotatably fits therein, shoulder means on said body portion engageable with said ring to inhibit inadvertent removal of said body portion from said ring member.

21. The applicator of claim 20 wherein said notch means includes a plurality of spaced notches around the perimeter of said base member, and said ring support includes a rigid lug adapted to engage with selective said notches.

22. The applicator of claim 21 further comprising an elongated continuous loop of dental floss with a tab affixed to said loop, said loop being of a size to extend from a looped end portion spanning between said pair of finger members of said floss stretcher through said passageway and another looped end portion about said post means and capable of being tightened to a taut condition by gripping with fingers of a user's hand while gripping around said handle, said tab being gripped by user's fingers to advance or retract said floss to a different spanning portion between said pair of finger members.

23. The applicator of claim 22 wherein said thimble includes a guideway engageable by floss when said stretcher is in said downright position.

24. The applicator of claim 23 wherein said post means includes a post extending laterally from each side wall of said handle and being generally aligned, one of said posts being engaged by a floss loop end when said stretcher is in said upright position and the other of said posts being engaged by a floss loop end when said stretcher is in said downright position.

25. A dental floss applicator comprising an L-shaped body including an elongated pistol grip having an upper and a lower end portion, an elongated arm having an elongated generally horizontal axis and end portion affixed to and extending forward from said grip upper end portion; a floss engaging post projecting laterally outwardly from said grip lower end portion, a support means rigidly attached to the opposite end portion of said arm; a floss stretching member selectively detachable to said support means, said floss stretching member including a base, means for rotatively positioning said base abot a generally vertical axis on said support means, said stretching member having two upwardly extending fingers attached to diametrically opposite sides of said base, each finger having a V-shaped depression in the upper extremity thereof.

26. The applicator of claim 25 further including selective means for releasable connecting said floss stretching member to said support means in a plurality of selected fixed orientations.

27. The applicator of claim 26 wherein said means for releasably connecting includes means on said support means and cooperating means on said base to selectively orient said base in a plurality of radially different positions of said stretching member to accommodate the various positions of teeth in a user's mouth.

28. The applicator of claim 27 wherein one said means and cooperating means includes a shoulder and the other said means and cooperating means includes a pair of shoulders engageable with said shoulder and preventing relative rotation between said support means and said base while so engaged.

29. The applicator of claim 28 wherein said cooperating means includes a plurality of notches in the perimeter of said base, said one means including at least two spaced projections, one of which interfits with one of said notches when said floss stretching member is in an upright position and the other of which interfits with one of said notches when said floss stretching member is in a downright position.

30. The applicator of claim 25 wherein said handle is offset so that a central plane through said handle and said arm is at an acute angle to a plane through the longitudinal axis of said arm and said floss stretcher to provide a comfortable position for a hand of a user during flossing of a user's teeth.

31. The applicator of claim 25 wherein said stretching member includes a passageway therethrough between said fingers, an elongated continuous loop of dental floss stretched spanningly over said V-shaped depression of said fingers and through said passageway and about said floss engaging post permitting a user to grip said floss loop adjacent to and forced toward said handle whereby said floss is stretched taut between said V-shaped depressions of said fingers.

32. The applicator of claim 31 wherein said loop of floss includes a tab attached to said loop to permit a user's fingers to grip same and advance or retract said floss in either direction between said fingers while said floss is not taut thereby positioning a clean floss section between said floss head fingers.

33. The applicator of claim 25 wherein said support means includes a thimble openingly facing toward said handle.

34. The applicator of claim 33 wherein said thimble includes a guideway engageable by floss when said stretching member is located in a downright position.

35. A dental floss applicator comprising an elongated pistol grip handle having a lower end portion and an upper end portion, a pair of posts projecting laterally from said lower end portion and adapted to receive a portion of the dental floss thereabout, an elongated arm having rearward and forward end portions, said rearward end portion being connected to said upper end portion and extending generally horizontally, a thimble member attached to said forward end portion and having a cavity therein opening rearwardly to receive an index fingertip therein of a hand gripping said handle, a ring support attached to and extending forwardly of said thimble member, a selectively attachable floss stretcher having a base member with a passageway therethrough and positioned within said ring support in an upright position and alternately in a downright position, a pair of spaced oppositely facing generally vertical finger members projecting from said base member and having bifurcated free ends adapted to receive a portion of floss therein, selective locating means between said base member and said ring support to selectively orient said base member in various rotative positions with respect to said ring support in either said upright and downright positions, and a continuous loop of dental floss having a portion spanning between said finger members and passing through said passageway in said base member and looped about one said post when said stretcher is in said upright position and looped about the other said post when said stretcher is in said downright position, said thimble including a guideway engageable by said floss when said stretcher is in said downright position.

* * * * *